United States Patent [19]

Dziabo et al.

[11] Patent Number: 4,997,626
[45] Date of Patent: Mar. 5, 1991

[54] METHODS TO DISINFECT CONTACT LENSES

[75] Inventors: Anthony J. Dziabo, El Toro; Hampar Karageozian, Laguna Hills; Paul S. Ripley, Irvine, all of Calif.

[73] Assignee: Allergan, Inc., Irvine, Calif.

[21] Appl. No.: 461,540

[22] Filed: Jan. 5, 1990

[51] Int. Cl.$^5$ .............................................. A61L 2/18
[52] U.S. Cl. ...................................... 422/37; 422/28; 422/29; 514/840
[58] Field of Search .......................... 422/28, 29, 37; 424/661, 662, 663, 665; 514/839, 840; 252/106

[56] References Cited

U.S. PATENT DOCUMENTS

| Re. 32,672 | 5/1988 | Huth et al. | 252/95 |
|---|---|---|---|
| 3,278,447 | 10/1966 | McNicholas | 252/187 |
| 3,910,296 | 10/1975 | Karageozian et al. | 134/2 |
| 3,912,451 | 10/1975 | Gaglia, Jr. | 21/58 |
| 4,084,747 | 3/1978 | Alliger | 239/4 |
| 4,104,190 | 8/1978 | Hartshorn | 424/663 X |
| 4,499,077 | 2/1985 | Stockel et al. | 424/149 |
| 4,557,925 | 12/1985 | Lindahl et al. | 424/19 |
| 4,568,517 | 2/1986 | Kaspar et al. | 422/30 |
| 4,614,549 | 9/1986 | Ogunbiyi et al. | 134/19 |
| 4,654,208 | 3/1987 | Stockel et al. | 424/78 |
| 4,689,215 | 8/1987 | Ratcliff | 424/53 |
| 4,767,559 | 8/1988 | Kruse et al. | 252/106 |

FOREIGN PATENT DOCUMENTS

| 0082798 | 6/1983 | European Pat. Off. |
| 0147100 | 7/1985 | European Pat. Off. |
| 0209071 | 1/1987 | European Pat. Off. |
| 0255041A1 | 2/1988 | European Pat. Off. |
| WO8504107 | 9/1985 | PCT Int'l Appl. |
| WO8605695 | 10/1986 | PCT Int'l Appl. |
| 2139260A | 11/1984 | United Kingdom |
| 2151039A | 7/1985 | United Kingdom |
| 2173017A | 10/1986 | United Kingdom |

OTHER PUBLICATIONS

Chemical Abstracts Selects: Issue 2, 1987, 106:9424f.

Primary Examiner—Robert J. Warden
Assistant Examiner—Jeffrey R. Snay
Attorney, Agent, or Firm—Gordon L. Peterson; Frank J. Uxa, Jr.

[57] ABSTRACT

A method for disinfecting a contact lens is disclosed. This method comprises contacting a contact lens to be disinfected in a liquid medium with chlorine dioxide present in an amount effective to disinfect the contact lens to be disinfected.

29 Claims, No Drawings

METHODS TO DISINFECT CONTACT LENSES

BACKGROUND OF THE INVENTION

This invention relates to disinfecting lenses, such as contact lenses. In particular, the invention relates to methods useful to quickly and effectively disinfect contact lenses.

Contact lenses should be periodically disinfected to protect the wearer's eyes from infection and to improve the wearer's comfort. It is often desirable that lens disinfecting be accomplished quickly, e.g., for the convenience of the wearer. However, conventional fast-acting disinfectants that are used with contact lenses have a high potential to cause eye irritation. A disinfectant which can be easily and effectively dissipated after use would be advantageous to reduce the chance of eye irritation.

Stockel et al U.S. Pat. No. 4,499,077 discloses an antimicrobial composition for soft contact lenses including an oxidizing agent such as an oxyhalogen compound, e.g., stabilized chlorine dioxide, or hydrogen peroxide, and a polymeric germicide, e.g., a quaternary ammonium polymer or an amino and/or imino polymer or salts thereof. Stockel et al U.S. Pat. No. 4,654,208 discloses an antimicrobial composition for contact lenses including an aqueous solution of a germicidal polymeric nitrogen compound and an oxidizing agent, e.g., chlorine dioxide, stabilized chlorine dioxide or hydrogen peroxide, to potentiate the activity of the germicidal polymeric nitrogen compound at low concentrations. The Stockel et al patents characterize the "polymeric germicides" and the "germicidal polymeric nitrogen compounds" as positively charged, nitrogen-containing cationic polymers, such as certain quaternary ammonium polymers and polymeric amino and/or imino compounds, e.g., polydiguanides. Neither of these Stockel et al patents relate to contact lens disinfecting compositions without such positively charged, nitrogen-containing cationic polymers.

In addition to being disinfected, the contact lens should be cleaned, e.g., of protein-based debris which accumulates on the lens during use. Such lens cleaning is often done in the presence of one or more enzymes. See, for example, Karageozian U.S. Pat. No. 3,910,296. In many instances, a complete lens maintenance procedure involves first enzymatic cleaning followed by a separate lens disinfecting step.

SUMMARY OF THE INVENTION

New methods for disinfecting, and preferably cleaning, lenses, in particular contact lenses, have been discovered. These methods utilize an amount of chlorine dioxide effective to disinfect the lens. Chlorine dioxide has been found to be a very effective contact lens disinfectant. The chlorine dioxide is effective as a contact lens disinfectant without requiring the presence of other germicides. Thus, chlorine dioxide can be the sole contact lens disinfectant. In addition, after the desired disinfecting has taken place, the contact lens can be effectively freed, e.g., by rinsing, neutralization, etc., of residual chlorine dioxide so as to reduce the chances of eye irritation when the disinfected contact lens is placed in the eye.

In one broad aspect, the invention involves a method for disinfecting a lens, e.g., a contact lens. A lens to be disinfected is contacted in a liquid medium with chlorine dioxide present in an amount effective to disinfect the lens to be disinfected. The liquid medium is substantially free of quaternary ammonium salts and positively charged, nitrogen-containing cationic polymers, such as those discussed in the above-noted Stockel et al patents. This contacting results in the lens being disinfected. After disinfection, the disinfected lens may be placed directly in the eye. Alternately, a simple saline rinse and/or soak of the disinfected lens may be employed before placing the lens in the eye.

In another broad aspect of the invention, the disinfected contact lens or the contact lens to be disinfected is contacted with at least one enzyme capable of removing protein-based debris from a contact lens in an amount effective to remove protein-based debris from the disinfected contact lens or the contact lens to be disinfected. This removal or cleaning step is preferably conducted before the disinfecting step.

Overall, the present invention is very effective and easy to use. This encourages the lens wearer to disinfect, and preferably clean, his/her contact lenses frequently, resulting in more comfort and less eye irritation.

DETAILED DESCRIPTION OF THE INVENTION

The present system is applicable for disinfecting all types of lenses, e.g., contact lenses, which are benefited by periodical disinfecting. Such lenses may be made of any material or combination of materials and may have any suitable configuration.

One important feature of the present invention is the use of chlorine dioxide per se as the lens disinfectant. Preferably, the disinfecting is performed by chlorine dioxide in a liquid medium. Thus, chlorine dioxide itself may be dissolved in the liquid medium and used to disinfect the lens. However, it is often impractical or even impossible to dissolve sufficient gaseous chlorine dioxide in a liquid medium, e.g., saline, to be an effective contact lens disinfectant. In addition, the dissolved chlorine dioxide is often very rapidly lost from the liquid medium.

In order to avoid these concerns, the liquid medium may, and preferably does, initially include at least one "precursor" of chlorine dioxide. Such precursors act in the liquid medium in response to one or more factors other than the presence of the lens to be disinfected to produce chlorine dioxide in a lens disinfecting amount. Chlorine dioxide per se and not, for example, a chlorine dioxide precursor, acts as the primary, preferably as the sole, disinfecting agent to disinfect the lens. As used herein, a disinfecting amount of chlorine dioxide means such amount as will reduce the microbial burden or load by one log order in 3 hours or less, preferably in 1 hour or less, and more preferably in 10 minutes or less.

The liquid medium is substantially free of any quaternary ammonium salts, and positively charged, nitrogen-containing cationic polymers, such as those disclosed as having antimicrobial or germicidal properties in the above-noted Stockel et al patents. Among the positively charged, nitrogen-containing cationic polymers which have antimicrobial or germicidal properties are quaternary ammonium polymers, such as copolymers of at least one mono-or di-functional tertiary amine and a dihalo organic compound. Also included in such positively charged, nitrogen-containing cationic polymers are polymeric amino and/or imino compounds, such as polydiguanides.

Preferably, the liquid medium, in particular the liquid aqueous medium, used in the present chlorine dioxide contacting step is substantially free of any and all antimicrobial agents (meaning to include therein germicides) other than chlorine dioxide and one or more precursors of chlorine dioxide. As used herein, the term "antimicrobial agent" means a material which when included in liquid water at a concentration similar to the concentration of known effective, non-oxidative contact lens disinfectants in aqueous contact lens disinfecting solutions, for example at a concentration of 0.6% by weight or less, or even at a concentration of 0.2% by weight or less, is itself an effective contact lens disinfectant, i.e., is effective to reduce the microbial burden or load by one log order in 3 hours or less, preferably in 1 hour or less, and more preferably in 10 minutes or less.

In general, the chlorine dioxide precursors useful in the present invention are those which form or produce chlorine dioxide in a liquid medium, preferably a liquid aqueous medium, in response to at least one factor other than the presence of the lens to be disinfected. For example, such chlorine dioxide precursors may form or produce chlorine dioxide in the presence of certain metal-containing components or in a reduced pH environment. The use of metal containing-components to promote chlorine dioxide formation from chlorine dioxide precursors is more fully described in commonly assigned U.S. Pat. Application Ser. No. 416,074 filed Oct. 2, 1989. The use of reduced pH to activate chlorine dioxide precursors to produce chlorine dioxide is more fully described in commonly assigned U.S. Pat. Application Ser. No. 461,405, filed Jan. 5, 1990. Each of these applications is incorporated in its entirety by reference herein.

One method for generating chlorine dioxide in an aqueous medium comprises buffering the medium to between pH 6-10, and exposing a stable chlorine dioxide precursor to a transition metal for at least one minute.

Any transition metal capable of effecting the release of chlorine dioxide from the precursor in an aqueous medium at a pH between 6-10, or possibly higher, may be employed. The primary criteria for such transition metal is that it have the ability to effect formation of a disinfecting amount of chlorine dioxide from the described chlorine dioxide precursors. Such metals should also have no substantial detrimental effect on the lens to be disinfected.

It is preferred that the metal component be present as a solid. In certain embodiments, solid metals can be easily and conveniently introduced into or removed from the chlorine dioxide precursor-containing liquid medium, as desired. Also a solid metal component can be readily separated from the solution for repeated use in disinfecting lenses. The metal may be immobilized, or maintained substantially stationary, relative to the solution.

The particular metals of interest herein are the transition metals and mixtures thereof, in particular from Group III metals, Group IV metals, Group V metals, Group VI metals, Group VII metals, Group VIII metals and mixtures thereof.

Because of their high degree of effectiveness, platinum group metals and mixtures thereof, and especially platinum, are particularly useful. The platinum group metals include platinum, palladium, iridium, ruthenium, rhodium and osmium.

The metal or metals may be present in the metallic form and/or in a combined form as part of an organic or inorganic compound or complex.

The amount of metal needed to practice this invention is to be viewed in terms of what quantity or surface area is useful to generate a particular concentration of chlorine dioxide in a given time and in light of the amount of precursor present in solution. It has been observed that the metal is not used up in the process of generating chlorine dioxide. Thus it is assumed the metal acts as a catalyst to effect formation of the chlorine dioxide. But the chemistry has not been investigated other than to observe that the metal apparently is not consumed in the process of creating chlorine dioxide.

Assuming the process is catalytic in nature, the amount of metal surface area exposed to the solution should be taken into consideration. Specific surface area data can be readily determined by simply exposing a chlorite salt of one concentration to various metals deposited on different surface area, then observing the rate of chlorine dioxide formation. From there, actual working parameters can be generated. Transition metals useful herein can also be dispersed in the aqueous medium.

It is most convenient to place the metals on some support device. Such supports are particularly useful if the metal includes one or more platinum group metals, which are quite expensive. The support may be chosen so as to provide surface area on which the promotion component can be placed.

Any suitable support material may be employed, and preferably is substantially inert at the conditions employed in the present invention. Examples of support materials include polymeric materials (plastics), metals, aluminas, silicas, clays, ceramics and the like. The supported promotion component may have any suitable shape or configuration, such as sheets, rods, extrudates, tablets, pills, irregular shaped particulars, spheres, disks and the like. Any of a number of conventional techniques can be employed to deposit the metal-containing component on the support material. These techniques include impregnation, co-precipitation, ion-exchange, dipping, spraying, vacuum depositions and the like.

During the disinfecting contacting, it is preferred that the aqueous medium have a pH in the range of about 6 to 10, but more preferably about 7.5. Such more preferred pH ranges are substantially consistent with the normal physiological pH for humans. Thus, after disinfecting, the disinfected lens may be placed directly in the eye.

This invention may be practiced at a pH lower than 6. At that pH, and lower, chlorine dioxide is generated from chlorites and many stabilized chlorine dioxides by virtue of the lower pH. In essence, the precursor is not stable for very long at these lower pHs at standard temperature and pressure. So formulating a composition for use at some remote time such as is often encountered with consumer products where the shelf life of the product must be many months means this aspect of the invention has certain formulation limitations. But is has been found that a transition metal will increase the amount of chlorine dioxide generated at lower pHs, as well as the rate at which it is generated. If such highly acidic conditions are employed, a neutralization step may be useful to neutralize any acidic residue which may remain in or on the lens. Neutralization can be easily accomplished by rinsing or soaking the disinfected lens in a neutral or slightly basic saline solution.

Alternately, a lens to be disinfected is contacted with a composition including a liquid medium and at least one chlorine dioxide precursor, which contacting takes place in the presence of at least one acidic component in an amount to effect formation of chlorine dioxide from the precursor. This contacting results in the lens being disinfected. Thus, in mildly acidic conditions, in particular at a pH of less than about 6 and especially in the range of about 3 to about 5, the production of chlorine dioxide is effected.

Any suitable acidic component may be employed. The primary criteria for such component is that it have the ability to increase the acidity of the liquid medium containing at least one chlorine dioxide precursor sufficiently to effect formation of chlorine dioxide from such chlorine dioxide precursor, and preferably sufficiently to effect formation of lens disinfecting amounts of chlorine dioxide from the presently useful chlorine dioxide precursors. Such acidic components should also have no substantial detrimental effect on the lens to be disinfected.

Examples of the presently useful acidic components include mineral acids, salts of such mineral acids, carboxylic acids, salts of such carboxylic acids and mixtures thereof. The mineral acids include, for example, nitric acid, sulfuric acid, hydrogen halides, phosphoric acid and the like. The carboxylic acids include both mono- and poly-, e.g., di-, tri- and the like, carboxylic acids, and preferably include 1 to about 10 carbon atoms per molecule. One or more non-hydrocarbonaceous groups, e.g., hydroxy groups, halide groups and the like, may be appended to the carboxylic acid. If an acid salt is employed, it is preferred that the salt be an alkali or alkaline earth metal salt, more preferably an alkali metal salt. A particularly useful group of acidic components is selected from alkali metal hydrogen phosphates, citric acid, lactic acid, tartaric acid and mixtures thereof.

During the disinfecting contacting, it is preferred that the liquid aqueous medium have a pH of about 6 or less, in particular in the range of about 3 to about 5.

After the disinfecting contacting, the disinfected lens is contacted with a liquid medium having reduced acidity relative to the liquid medium in the disinfecting contacting. For example, the disinfected lens can be contacted with e.g., rinsed and/or soaked in, a second liquid medium, e.g., a conventional saline or buffered saline solution, separate and apart from the liquid medium, the first liquid medium, used in the disinfecting contacting. The second liquid medium has reduced acidity relative to the liquid medium used in the disinfecting contacting. Alternately, the acidity of the liquid medium used in disinfecting contacting can be reduced in an acidity adjusting step, as described herein. In any event, after the acidity is reduced, the disinfected lens is preferably present in a liquid aqueous medium which preferably has a pH in the range of about 6.5 to about 8, and more preferably about 7.5. Such pH ranges are substantially consistent with the normal physiological pH for humans. Thus, after disinfecting and acidity reduction, the disinfected lens may be placed directly in the eye. Alternately, a simple saline rinse of the disinfected lens may be employed before placing the lens in the eye. This is in contrast to other systems which require elaborate neutralization procedures before the lens is suitable for placement in the eye.

The present acidity adjusting step preferably provides for reducing the acidity of the liquid medium containing the disinfected lens. Thus, if the liquid medium is aqueous-based, the adjusting step preferably provides for increasing the pH of the disinfected lens-containing liquid medium. In one embodiment, an acidity adjusting component useful to reduce the acidity of the liquid medium is introduced into the liquid medium after the lens has been disinfected. However, this acidity adjusting component may be introduced into the liquid medium at substantially the same time as is the acidic component introduced into the liquid medium. The acidity adjusting component can be included in a delayed release form, e.g., tablet, pill or the like, designed to release the acidity adjusting component into the liquid medium after the pill or tablet is exposed to the liquid medium. For example, the acidity adjusting component can be included in a composition with the acidic component with the composition structured to release the acidity adjusting component into a liquid medium after the acidic component is released into the liquid medium.

The acidity adjusting component is preferably selected from the group consisting of basic components, buffer components and mixtures thereof. The acidity adjusting component may be a mixture of at least one basic component and at least one buffer component. The acidity adjusting component should have no substantial detrimental effect on the lens being treated. Examples of the presently useful acidity adjusting components include borates, dibasic phosphates, carbonates, bicarbonates, mixtures thereof and the like. The acidity adjusting components preferably are compounds including alkali metals or alkaline earth metals, in particular alkali metals, especially sodium.

The amount of the acidity adjusting component or components employed is sufficient to achieve the desire acidity reduction in the liquid medium containing the disinfected lens.

Among the preferred chlorine dioxide precursors useful in the present invention is stabilized chlorine dioxide. The term "stabilized chlorine dioxide" as used herein means one or more chlorine dioxide-containing complexes and/or one or more chlorite-containing components and/or one or more other entities capable of forming chlorine dioxide in a liquid medium in response to at least one factor other than the presence of the lens to be disinfected.

Examples of such chlorite-containing components include metal chlorites, and in particular alkali metal and alkaline earth metal chlorites. A specific example of a chlorite-containing component which is useful as a chlorine dioxide precursor is technical grade sodium chlorite. Among the preferred chlorine dioxide-containing complexes are complexes of chlorine dioxide with carbonate, chlorine dioxide with bicarbonate and mixtures thereof. The exact chemical composition of many of the chlorine dioxide precursors, e.g., stabilized chlorine dioxide, and in particular the chlorine dioxide complexes, is not completely understood. The manufacture or production of certain chlorine dioxide precursors is described in McNicholas U.S. Pat. No. 3,278,447, which is hereby incorporated in its entirety by reference herein. Specific examples of useful chlorine dioxide precursor sources include products such as that sold under the trademark Dura Klor by Rio Linda Chemical Company, Inc., and that sold under the trademark Anthium Dioxide by International Dioxide, Inc. An especially useful chlorine dioxide precursor source is a product sold under the trademark Purogene by BioCide International, Inc. The chlorine dioxide precursor may be included in a liquid medium at a predetermined concentration, e.g., a concentration chosen to provide a disinfecting amount of chlorine dioxide in response to at least one factor other than the presence of the lens to be disinfected. Preferably, the liquid medium has sufficient chlorine dioxide precursor so as to have a potential of producing chlorine dioxide in the range of about 0.002% to about 3% by weight, based on the total weight of the liquid medium including the chlorine dioxide precursor or precursors.

In one embodiment, the chlorine dioxide precursor includes a functionality selected from carbonate, borate, sulfate, phosphate, and mixtures thereof.

The liquid medium used is selected to have no substantial detrimental effect on the lens being treated and to allow, and preferably to even facilitate, the present lens treatment or treatments. The liquid medium is preferably aqueous-based. A particularly useful liquid aqueous medium is that derived from saline, e.g., a conventional saline solution.

The disinfecting contacting preferably occurs at a temperature to maintain the liquid medium substantially liquid. For example, when the liquid medium is aqueous-based, it is preferred that the contacting temperature be in the range of about 0° C. to about 100° C., and more preferably in the range of about 10° C. to about 60° C. Contacting at or about ambient temperature is very convenient and useful. The contacting preferably occurs at or about atmospheric pressure. This contacting preferably occurs for a time to substantially completely disinfect the lens being treated. Such contacting times can be in the range of about 0.1 hours to about 12 hours or more.

In order to insure that the pH of the liquid aqueous medium is maintained within the desired range during the disinfecting procedure, the liquid aqueous medium may include at least one buffer component. Although any suitable buffer component may be employed, if a chlorine dioxide precursor is employed it is preferred to select such component so as not to substantially detrimentally affect the desired formation of chlorine dioxide. It is preferred that the buffer component be inorganic.

Among the preferred buffer components are those which include phosphate functionalities, borate functionalities, carbonate functionalities and mixtures thereof. Particularly increased rates of chlorine dioxide formation are achieved when the buffer component includes phosphate functionalities, borate functionalities and mixtures thereof. Alkali metal and alkaline earth metal buffer components are advantageously used in the present invention.

In one embodiment, the lens is subjected to the action of at least one enzyme to remove debris in addition to disinfecting the lens. This enzyme/lens contacting occurs in a liquid medium, preferably an aqueous liquid medium, such as described elsewhere herein. Among the types of debris that form on contact lens during normal use are protein-based debris, mucin-based debris, lipid-based debris and carbohydrate-based debris. One or more types of debris may be present on a single contact lens.

The enzyme or enzymes used are capable of removing at least one type of debris from a contact lens. The amount of such enzyme or enzymes used is effective to remove substantially all of at least one type of debris from a debris laden contact lens in a reasonable time, preferably in the range of about 1 minute to about 12 hours. The active enzyme-containing liquid medium preferably contains sufficient enzyme to provide between about 0.0001 to about 5 Anson units of activity, more preferably between about 0.01 to about 1 Anson units, per single lens treatment.

The enzyme employed may be selected from enzymes which are conventionally employed in the enzymatic cleaning of contact lenses. For example, many of the enzymes disclosed in Huth et al Reissue U.S. Pat. No. 32,672 are useful in the present invention. This patent is incorporated in its entirety by reference herein. Among the useful enzymes are those selected from proteolytic enzymes, lipases and mixtures thereof., The enzyme may be one or more carbohydrate-active enzymes such as carbolytic enzymes. Specific examples of useful enzymes include proteases, amylases, lipases and mixtures thereof.

The cleaning action of the enzyme may occur prior to or after the chlorine dioxide disinfecting of the lens. In one embodiment, the liquid medium which includes the chlorine dioxide precursor also includes the enzyme. If the precursor is present during the enzyme cleaning, the precursor should be maintained so that substantially no chlorine dioxide is formed. After sufficient time for effective enzymatic cleaning of the lens has elapsed, the precursor is promoted, activated or otherwise induced to produce chlorine dioxide to disinfect the enzymatically cleaned lens. Alternately, the enzyme can be present in a delayed release form together with a chlorine dioxide neutralizing component, e.g., an acidity adjusting component such as a basic or buffer component. In this embodiment, the enzyme is released after the lens in disinfected. Thus, the enzyme is released at substantially the same time or after the chlorine dioxide neutralizing component and acts to clean the disinfected lens with no substantial interference from chlorine dioxide.

The following non-limiting examples illustrate certain aspects of the present invention.

EXAMPLE 1

This example illustrates the effect of stabilized chlorine dioxide concentration on the production of chlorine dioxide.

A series of solutions was prepared using different concentrations of a stabilized chlorine dioxide product, sold by Bio-cide International, Inc. under the trademark Purogene. The stabilized chlorine dioxide product included 2.0% by weight of potential (ultimate yield) chlorine dioxide and 0.085% by weight of sodium carbonate.

Each of these solutions was prepared as follows:
(1) 0.1% (W/V) of boric acid was dissolved in deionized water to provide buffering;
(2) a calculated amount of sodium chloride was added so that the final solution was isotonic;
(3) the pH of the solution was adjusted to 7.5;
(4) the desired amount of the stabilized chlorine dioxide product was added; and
(5) the final volume of the solution was adjusted using deionized water.

Each of these solutions was tested as follows. A 10 ml. sample of the solution was placed in a plastic container at ambient temperature and pressure. A plastic disc, containing platinum as platinum oxide, was placed in the container in the solution. The actual concentration of chlorine dioxide in the solution was monitored at various times after the disc was placed in the container. Results of these tests were as follows:

TABLE 1

| | Stabilized ClO₂ Product Concentrations, ppm by wt. | | | | | |
|---|---|---|---|---|---|---|
| Time (min) | 0.0 | 50 | 100 | 250 | 500 | 750 | 1000 |
| | ClO₂ Concentration, ppm by wt. | | | | | |
| 0 | 0.0 | 0.00 | 0.00 | 0.00 | 0.00 | 0.00 | 0.00 |
| 30 | 0.0 | 0.74 | 0.99 | 1.80 | 3.76 | 6.40 | 6.31 |
| 60 | 0.0 | 0.94 | 1.61 | 5.11 | 6.11 | 8.19 | 10.79 |
| 90 | 0.0 | 1.09 | 1.66 | 3.72 | 10.93 | 8.46 | 12.28 |
| 120 | 0.0 | 0.90 | 1.81 | 4.06 | 12.08 | 11.80 | 12.78 |
| 240 | 0.0 | 1.13 | 1.26 | 4.95 | 8.10 | 11.18 | 19.19 |
| 480 | 0.0 | 1.00 | 1.28 | 4.08 | 5.17 | 10.23 | 13.78 |

These results indicate that the concentration of chlorine dioxide reaches a maximum and then begins to decrease with time. Further, the initial pH of each solution was about 7.5 and remained substantially unchanged throughout the test.

It has been reported that essentially no chlorine dioxide was detected in a borate buffered, 0.85% sodium chloride aqueous solution containing the above-noted stabilized chlorine dioxide product at a pH of 7.5. Thus, these results do demonstrate that platinum does effect formation of chlorine dioxide.

EXAMPLE 2

A solution containing deionized water, 0.85% (w/v) of sodium chloride, 0.10% (w/v) of boric acid, and 50 ppm w/v of the stabilized chlorine dioxide product identified in Example 1 was prepared. Each of the concentrations of stabilized chlorine dioxide product set forth in Examples 2 and 3 is stated in terms of potential chlorine dioxide. One portion of this solution was buffered to a pH of 7.9, while the other portion was buffered to a pH of 6.8. Varying amounts of tartaric acid was added to different samples of each of these portions. The samples were then tested, following the standard procedure, to determine the D-value with respect to various microorganisms. The D-value is defined as the length of time required to reduce the microbial burden or load by one log unit.

Results of these tests were as follows:

TABLE 2

| Tartaric Acid, ppm | 30 | 40 | 50 | 60 | 70 |
|---|---|---|---|---|---|
| Microorganism | Extrapolated D-value at 23° C., min | | | | |
| pH = 6.8 | | | | | |
| Free Chlorine Dioxide, ppm | 10.74 | 17.08 | 37.94 | 25.38 | 32.47 |
| S. marcescens | <84 | <84 | <84 | <84 | <84 |
| S. aureus | <87 | <87 | <87 | <87 | <87 |
| P. aeruginosa | <85 | <85 | <85 | <85 | <85 |
| A. fumigatus | <83 | <83 | <83 | <83 | <83 |
| pH = 7.9 | | | | | |
| Free Chloride Dioxide, ppm | 0.03 | 0.11 | 0.05 | 0.15 | 0.23 |
| S. marcescens | 5.13 | <85 | 2.56 | <85 | 2.56 |
| S. aureus | 10.17 | 2.54 | 2.54 | 12.24 | 2.54 |
| P. aeruginosa | 19.48 | <87 | 2.6 | <87 | <87 |
| A. fumigatus | 109 | 109 | 150 | 162.2 | 70.6 |

These results of Examples 1 and 2 indicate that chlorine dioxide per se can be present in a sufficient amount in a liquid medium to be effective to disinfect contact lenses. Thus, these results demonstrate that sufficient chlorine dioxide can be provided in a liquid medium to reduce the microbial burden or load by one log order in a period of time generally deemed acceptable for disinfecting contact lenses.

EXAMPLE 3

A lens disinfecting system was provided which included a solution, an activator tablet and a neutralizer tablet.

The solution was purified water with the following components: 0.85% (w/v) sodium chloride; 0.10% (w/v) boric acid; and 0.005% (w/v) the stabilized chlorine dioxide product identified in Example 1. The pH of this solution is about 7.7 to 7.9.

The activator tablet had the following composition: 27.0 mg. tartaric acid; 10.0 mg. anhydrous sodium carbonate; 40.6 mg. sugar-based binder/filler; and 2.4 mg. polyethylene glycol (molecular weight of about 3350) (a conventional tableting lubricant).

The neutralizer tablet had the following composition: 3.0 mg. tartaric acid; 21.0 mg. sodium carbonate; 23.3 mg. sugar-based binder/filler; 1.5 mg. polyethylene glycol (molecular weight of about 3350); and 1.2 mg. N-acetylcysteine.

The activator tablet was placed in 10 ml. of the solution and the resulting material was monitored for pH and chlorine dioxide concentration. Chlorine dioxide appeared in 28±3 seconds. The pH of the material was noted at 3.6±0.1. After 5 minutes, the chlorine dioxide concentration was 43.62±0.38 ppm. After 30 minutes, the chlorine dioxide concentration was 41.12±0.92 ppm.

The neutralizer tablet was then placed in the material. The neutralizer tablet dissolved in the material. Upon shaking the material, the characteristic color of chlorine dioxide which was present disappeared immediately. The pH of the final solution was 6.61±0.03 and drifted up to about 7 after 30 minutes. The chlorine dioxide concentration of the final solution is 0.16±0.04 ppm.

The amount of chlorine dioxide produced by combining the activator tablet with the solution is effective to kill most microorganisms in about 10 minutes or less, e.g., about 1 to 2 minutes. Disinfection of soft contact lens can be accomplished in about 1 to 2 minutes. However, at this point, the solution has a disagreeable odor and color, a low pH and may contain sufficient chlorine dioxide to cause eye irritation.

The neutralizer tablet is added to the solution to raise the pH to a comfortable level and consume chlorine dioxide. A disinfected contact lens could be taken from the neutralized system and placed directly in the eye without irritation or discomfort. Alternately, the disinfected contact lens could be removed from the chlorine dioxide-containing solution and contacted, e.g., washed, with a buffered saline solution prior to being placed into the eye.

While this invention has been described with respect to various specific examples and embodiments, it is to be understood that the invention is not limited thereto and that it can be variously practiced within the scope of the following claims.

What is claimed is:

1. A method for disinfecting a contact lens which comprises:
    contacting a contact lens in a liquid medium with chlorine dioxide present in an amount as other than a chlorine dioxide precursor liquid medium being substantially free of quaternary ammonium salts and positively charged, nitrogen-containing cationic polymers.

2. The method of claim 1 wherein said liquid medium includes at least one buffer component.

3. The method of claim 1 wherein said liquid medium is an aqueous liquid medium which is substantially free of antimicrobial agent other than chlorine dioxide and one or more precursors of chlorine dioxide.

4. The method of claim 3 wherein said contacting occurs at a temperature in the range of about 0° C. to about 100° C.

5. The method of claim 3 wherein said contacting occurs for a time in the range of about 1 minute to about 12 hours.

6. The method of claim 1 which further comprises contacting said contact lens with at least one enzyme capable of removing debris from a contact lens in an amount effective to substantially remove at least one type of debris from said contact lens.

7. The method of claim 6 wherein each of said at least one enzyme is selected from the group consisting of proteolytic enzymes, lipases and mixtures thereof.

8. The method of claim 6 wherein each of said at least one enzyme is selected from the group consisting of carbohydrate-active enzymes and mixtures thereof.

9. The method of claim 6 wherein each of said at least one enzyme is selected from the group consisting of proteases, amylases, lipases and mixtures thereof.

10. A method for disinfecting a contact lens which comprises:
contacting a contact lens in a liquid medium with chlorine dioxide present in an amount effective to disinfect said contact lens, said chlorine dioxide being derived from at least one chlorine dioxide precursor present in said liquid medium prior to said contacting which precursor is activated other than by the presence of said contact lens to produce said chlorine dioxide, said liquid medium being substantially free of quaternary ammonium salts and positively charged, nitrogen-containing cationic polymers.

11. The method of claim 10 wherein said liquid medium includes at least one buffer component.

12. The method of claim 10 wherein said chlorine dioxide precursor is stabilized chlorine dioxide.

13. The method of claim 10 wherein said chlorine dioxide precursor is selected from the group consisting of chlorine dioxide-containing complexes and mixtures thereof.

14. The method of claim 10 wherein said chlorine dioxide precursor is selected from the group consisting of complexes of chlorine dioxide and carbonate, complexes of chlorine dioxide and bicarbonate and mixtures thereof.

15. The method of claim 10 wherein said chlorine dioxide precursor is selected from the group consisting of chlorite-containing components and mixtures thereof.

16. The method of claim 10 wherein said chlorine dioxide precursor includes a functionality selected from the group consisting of carbonate, borate, sulfate, phosphate and mixtures thereof.

17. The method of claim 10 wherein said liquid medium is an aqueous liquid medium which is substantially free of antimicrobial agent other than chlorine dioxide and one or more precursors of chlorine dioxide.

18. The method of claim 11 wherein said contacting occurs at a temperature in the range of about 0° C. to about 100° C.

19. The method of claim 17 wherein said contacting occurs for a time in the range of about 1 minute to about 12 hours.

20. The method of claim 10 which further comprises contacting said contact lens with at least one enzyme capable of removing debris from a contact lens in an amount effective to substantially remove at least one type of debris from said contact lens.

21. The method of claim 20 wherein each of said at least one enzyme is selected from the group consisting of proteolytic enzymes, lipases and 22. The method of claim 20 wherein each of said at least one enzyme is selected from the group consisting of carbohydrate-active enzymes and mixtures thereof.

23. The method of claim 20 wherein each of said at least one enzyme is selected from the group consisting of proteases, amylases, lipases and mixtures thereof.

24. The method of claim 10 wherein prior to said contacting with chlorine dioxide said contact lens is contacted with at least one enzyme capable of removing debris from a contact lens in an amount effective to substantially remove at least one type of debris from said contact lens.

25. The method of claim 24 wherein each of said at least one enzyme is selected from the group consisting of proteolytic enzymes, lipases and mixtures thereof.

26. The method of claim 24 wherein each of said at least one enzyme is selected from the group consisting of carbohydrate-active enzymes and mixtures thereof.

27. The method of claim 24 wherein each of said at least one enzyme is selected from the group consisting of proteases, amylases, lipases and mixtures thereof.

28. The method of claim 24 wherein each of said at least one enzyme contacting occurs in a liquid medium including said chlorine dioxide precursor.

29. The method of claim 24 wherein said at least one enzyme contacting occurs in a liquid medium in the substantial absence of said chlorine dioxide precursor.

* * * * *

UNITED STATES PATENT AND TRADEMARK OFFICE
CERTIFICATE OF CORRECTION

PATENT NO. : 4,997,626  Page 1 of 2
DATED : March 5, 1991
INVENTOR(S) : Anthony J. Dziabo, Hampar Karageozian, Paul Ripley It is certified that error appears in the above-identified patent and that said Letters Patent is hereby corrected as shown below:

Column 4, line 21, change "area" to -- areas -- .

Column 6, line 37, change "desire" to -- desired -- .

Column 9, lines 46-61, please delete "table 2" in its entirety and replace it with Table 2 as below:

TABLE 2 pH = 6.8

| | | | | | |
|---|---|---|---|---|---|
| Tartaric Acid, ppm. | 30 | 40 | 50 | 60 | 70 |
| Free Chlorine Dioxide, ppm. | 10.74 | 17.08 | 37.94 | 25.38 | 32.47 |
| Microorganism | Extrapolated D-value at 23°C., min. | | | | |
| S. marcescens | <.84 | <.84 | <.84 | <.84 | <.84 |
| S. aureus | <.87 | <.87 | <.87 | <.87 | <.87 |
| P. aeruginosa | <.85 | <.85 | <.85 | <.85 | <.85 |
| A. fumigatus | <.83 | <.83 | <.83 | <.83 | <.83 | pH = 7.9

| | | | | | |
|---|---|---|---|---|---|
| Tartaric Acid, ppm. | 30 | 40 | 50 | 60 | 70 |
| Free Chloride Dioxide, ppm. | 0.03 | 0.11 | 0.05 | 0.15 | 0.23 |
| Microorganism | Extrapolated D-value at 23°C., min. | | | | |
| S. marcescens | 5.13 | <.85 | 2.56 | <.85 | 2.56 |
| S. aureus | 10.17 | 2.54 | 2.54 | 12.24 | 2.54 |
| P. aeruginosa | 19.48 | <.87 | 2.6 | <.87 | <.87 |
| A. fumigatus | 109 | 109 | 150 | 162.2 | 70.6 |

UNITED STATES PATENT AND TRADEMARK OFFICE
CERTIFICATE OF CORRECTION

PATENT NO. : 4,997,626
DATED : March 5, 1991
INVENTOR(S) : Anthony J. Dziabo, Hampar Karageozian, Paul S. Ripley It is certified that error appears in the above—identified patent and that said Letters Patent is hereby corrected as shown below:

Column 10, line 61, through column 10, line 68, claim 1 of the patent, please replace as follows:

-- 1. A method for disinfecting a contact lens which comprises:

contacting a contact lens in a liquid medium with chlorine dioxide as other than a chlorine dioxide precursor present in an amount effective to disinfect said contact lens and thereby effectively disinfecting said contact lens, said liquid medium being substantially free of quaternary ammonium salts and positively charged, nitrogen-containing cationic polymers. --

Column 12, line 26, delete", lipases and" and insert in place thereof -- and lipases. --

Signed and Sealed this

Twenty-eighth Day of September, 1993

*Attest:*

BRUCE LEHMAN

*Attesting Officer*     *Commissioner of Patents and Trademarks*